(12) United States Patent
Klumb et al.

(10) Patent No.: US 6,248,122 B1
(45) Date of Patent: Jun. 19, 2001

(54) CATHETER WITH CONTROLLED RELEASE ENDOLUMINAL PROSTHESIS

(75) Inventors: Katherine J. Klumb, Los Altos; Thomas J. Fogarty, Portola Valley; Kirti P. Kamdar, Sunnyvale, all of CA (US)

(73) Assignee: Vascular Architects, Inc., San Jose, CA (US)

( * ) Notice: Subject to any disclaimer, the term of this patent is extended or adjusted under 35 U.S.C. 154(b) by 0 days.

(21) Appl. No.: 09/258,542

(22) Filed: Feb. 26, 1999

(51) Int. Cl.$^7$ ............................ A61M 29/02; A61F 02/02

(52) U.S. Cl. .................... 606/194; 623/1.11; 604/96

(58) Field of Search ............................ 604/96, 101, 103, 604/171, 264, 280; 606/108, 191, 192, 194, 198; 623/1.11

(56) References Cited

U.S. PATENT DOCUMENTS

| | | | |
|---|---|---|---|
| 3,993,078 | 11/1976 | Bergentz et al. | 128/334 R |
| 4,553,545 | 11/1985 | Maass et al. | 128/341 |
| 4,665,918 | 5/1987 | Garza et al. | |
| 4,732,152 | 3/1988 | Wallsten et al. | |
| 4,760,849 | 8/1988 | Kropf | 128/341 |
| 4,771,773 * | 9/1988 | Kropf | 606/108 |
| 4,795,458 | 1/1989 | Regan | |
| 4,848,343 | 7/1989 | Wallsten et al. | |
| 4,875,480 | 10/1989 | Imbert | |
| 4,886,062 | 12/1989 | Wiktor | |
| 4,913,141 | 4/1990 | Hillstead | |
| 5,037,427 | 8/1991 | Harada et al. | |
| 5,147,370 | 9/1992 | McNamara et al. | |
| 5,201,757 | 4/1993 | Heyn et al. | |
| 5,242,399 * | 9/1993 | Lau et al. | 604/104 |
| 5,246,445 | 9/1993 | Yachia et al. | |
| 5,306,294 | 4/1994 | Winston et al. | |
| 5,360,401 | 11/1994 | Turnland | |
| 5,372,600 | 12/1994 | Beyar et al. | |
| 5,411,551 | 5/1995 | Winston et al. | |
| 5,443,500 | 8/1995 | Sigwart | |
| 5,476,505 | 12/1995 | Limon | |
| 5,534,007 * | 7/1996 | Germain et al. | 606/108 |
| 5,603,698 * | 2/1997 | Roberts et al. | 604/104 |

(List continued on next page.)

FOREIGN PATENT DOCUMENTS

| | | |
|---|---|---|
| 29721310 | 12/1998 | (DE) . |
| 627 201 A1 | 6/1993 | (EP) . |
| 893 108 A2 | 1/1999 | (EP) . |
| WO 94/16629 | 8/1994 | (WO) . |
| WO 94/22379 | 10/1994 | (WO) . |
| WO 97/07756 | 3/1997 | (WO) . |
| WO 98/22159 | 5/1998 | (WO) . |
| 98/47447 | 10/1998 | (WO) . |
| 98/57692 | 12/1998 | (WO) . |

*Primary Examiner*—Gene Mancene
*Assistant Examiner*—Michael B. Priddy
(74) *Attorney, Agent, or Firm*—James F. Hann; Haynes & Beffel LLP (57) ABSTRACT

A catheter (4) includes a hollow catheter shaft (18), an inflatable balloon (36) surrounding the catheter shaft distal portion, and an expandable endoluminal prosthesis, such as a stent graft (38, 40), surrounding the balloon. The stent is typically a coiled stent having distal ends (58, 48) slidably housed within stent end holders (56, 50) on the catheter shaft. The first stent end is released from its holder by inflating the balloon. The second stent end is selectively released from its holder by other than inflating the balloon, typically by a push wire (30) pushing the second stent end out of its holder. A sheath (8) is moveable between a first position surrounding the stent and a second position spaced-apart from the stent. The stent is prevented from assuming its expanded-diameter state by (1) the engagement of the stent ends with the catheter shaft through the stent end holders, and (2) the sheath being in its first position during the introducing step. The stent may be a straight stent (3 8) or a bifurcated stent (38D).

55 Claims, 8 Drawing Sheets

U.S. PATENT DOCUMENTS

| | | |
|---|---|---|
| 5,607,445 | 3/1997 | Summers . |
| 5,683,451 | 11/1997 | Lenker et al. . |
| 5,700,285 | 12/1997 | Myers et al. .............................. 623/1 |
| 5,709,703 * | 1/1998 | Lukic et al. ......................... 606/198 |
| 5,749,919 | 5/1998 | Blanc . |
| 5,772,668 * | 6/1998 | Summers et al. .................... 606/108 |
| 5,776,142 * | 7/1998 | Gunderson ........................... 606/108 |
| 5,797,952 | 8/1998 | Klein . |
| 5,810,871 * | 9/1998 | Tuckey et al. ....................... 606/198 |
| 5,824,053 | 10/1998 | Khosravi et al. . |
| 5,824,054 | 10/1998 | Khosravi et al. . |
| 5,836,966 | 11/1998 | Germain . |
| 5,843,092 * | 12/1998 | Heller et al. ......................... 606/108 |
| 5,935,135 * | 8/1999 | Bramfitt et al. ..................... 606/108 |
| 5,980,533 * | 11/1999 | Holman ................................ 606/108 |
| 6,019,779 * | 2/2000 | Thorud et al. ....................... 606/108 |
| 6,027,516 | 2/2000 | Kolobow et al. . |

* cited by examiner

CATHETER WITH CONTROLLED RELEASE ENDOLUMINAL PROSTHESIS

BACKGROUND OF THE INVENTION

The present invention provides devices and methods for the endoluminal placement of prostheses, particularly within the vascular system for the treatment of cardiovascular disease, such as vascular stenoses, dissections, aneurysms, and the like. The apparatus and methods, however, are also useful for placement in other body lumens, such as the ureter, urethra, biliary tract, gastrointestinal tract and the like, for the treatment of other conditions which may benefit from the introduction of a reinforcing or protective structure within the body lumen. The prostheses will be placed endoluminally. As used herein, "endoluminally" will mean placement by percutaneous or cutdown procedures, wherein the prosthesis is translumenally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial and subdlavian arteries, for access to the target site.

An endoluminal prosthesis typically comprises at least one radially expansible, usually cylindrical, body segment. By "radially expansible," it is meant that the body segment can be converted from a small diameter configuration (used for endoluminal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. Alternatively, the prosthesis can be self-expanding. Such self-expanding structures are provided by a temperature-sensitive superelastic material, such as Nitinol, which naturally assumes a radially expanded condition once an appropriate temperature has been reached. The appropriate temperature can be, for example, a temperature slightly below normal body temperature; if the appropriate temperature is above normal body temperature, some method of heating the structure must be used. Another type of self-expanding structure uses resilient material, such as a stainless steel or superelastic alloy, and forming the body segment so that it possesses its desired, radially-expanded diameter when it is unconstrained, e.g., released from radially constraining forces a sheath. To remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well-known in the art and do not comprise part of the present invention.

The dimensions of a typical endoluminal prosthesis will depend on its intended use. Typically, the prosthesis will have a length in the range from 0.5 cm to 10 cm, usually being from about 0.8 cm to 5 cm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 30 mm, preferably being in the range from about 3 mm to 15 mm for vascular applications.

One type of endoluminal prosthesis includes both a stent component and a graft component. These endoluminal prostheses are often called stent grafts. A stent graft is typically introduced using a catheter with both the stent and graft in contracted, reduced-diameter states. Once at the target site, the stent and graft are expanded. After expansion, the catheter is withdrawn from the vessel leaving the stent graft at the target site.

Grafts are used within the body for various reasons, such as to repair damaged or diseased portions of blood vessels such as may be caused by injury, disease, or an aneurysm. It has been found effective to introduce pores into the walls of the graft to provide ingrowth of tissue onto the walls of the graft. With larger diameter grafts, woven graft material is often used. In small diameter vessels, porous fluoropolymers, such as PTFE, have been found useful.

Coil-type stents can be wound about the catheter shaft in torqued compression for deployment. The coil-type stent can be maintained in this torqued compression condition by securing the ends of the coil-type stent in position on a catheter shaft. The ends are released by, for example, pulling on wires once at the target site. See, for example, U.S. Pat. Nos. 5,372,600 and 5,476,505. Alternatively, the endoluminal prosthesis can be maintained in its reduced-diameter condition by a sleeve; the sleeve can be selectively retracted to release the prosthesis. A third approach is the most common. A balloon is used to expand the prosthesis at the target site. The stent is typically extended past its elastic limit so that it remains in its expanded state after the balloon is deflated. One balloon expandable stent is the PALMAZ-SHATZ stent available from the CORDIS Division of Johnson & Johnson. Stents are also available from Arterial Vascular Engineering of Santa Rosa, Calif. and Guidant Corporation of Indianapolis, Ind.

SUMMARY OF THE INVENTION

The present invention simplifies the release of at least one portion of an endoluminal prosthesis, such as a stent, a graft, a stent graft or other endoluminal structure having mechanical scaffolding sufficient to maintain patency, from a catheter shaft by using the inflation of a balloon to release the one prosthesis portion from the catheter shaft. The endoluminal prosthesis is optionally delivered to the target site within an introducer sheath. At least one other prosthesis portion may be selectively released by the user, typically using a mechanical element such as a push wire. Reducing the number of push wires or other release mechanisms simplifies the construction of the catheter. By selectively permitting one prosthesis portion, typically an end of a stent, to expand before the entire prosthesis is permitted to expand, the prosthesis can be located at the target site more precisely than possible with conventional techniques. The invention also results in no or substantially no foreshortening of the prosthesis during deployment. The invention permits controlled release of the prosthesis and permits the prosthesis to be repositioned if initially out of position.

A catheter is used to place the prosthesis at a target site within the body, typically within a blood vessel. The catheter preferably includes a catheter shaft having a distal portion and defining an inflation lumen. An inflatable balloon is preferably fluidly connected to the inflation lumen and typically surrounds the catheter shaft at its distal portion. A stent or other prosthesis, having first and second ends, surrounds the balloon. Graft material, typically in the form of porous PTFE or ePTFE, is used in the case of a stent graft. The graft material preferably surrounds the stent, or is positioned within and is attached to the stent, or is both positioned within and surrounding the stent.

The prosthesis has portions, typically ends, which are removably secured to the catheter shaft. When the prosthesis includes a stent, the stent may be of any conventional or other design; the stent is typically a coil-type stent having first and second distal ends. The ends of the stent are, in one preferred embodiment, slidably housed within first and second stent end holders carried by the catheter shaft. The first stent end holder is designed so that upon inflation of the balloon, the first stent end is released from the first stent end holder by the act of inflating the balloon. The second stent end is selectively released from the second stent end holder by other than inflating the balloon. For example, the second stent end may be released from the second stent end holder by movement of a wire along the catheter shaft which pushes the second stent end from the second stent end holder.

A sheath is preferably slidably mounted around the catheter shaft and is moveable between a first position surrounding the prosthesis and a second position spaced-apart from the prosthesis. Accordingly, when a sheath is used the prosthesis is initially prevented from assuming its second, expanded-diameter state by (1) the removable securement of the first and second prosthesis portions with the catheter shaft, and (2) the sheath being in its first position during the introducing step. After the distal catheter portion has been introduced to the target site within the body, the sheath is pulled back to its second position thus exposing the prosthesis.

A preferred method for releasing the first and second ends of a prosthesis, in particular a coil-type stent, starts by first partially inflating the balloon causing the first end of the stent to be released from the catheter shaft. The balloon is then at least partially deflated to permit the coiled, torqued stent to at least partially unwind and expand radially outwardly. The balloon is then reinflated to be at least substantially fully inflated and the second stent end is released from the second stent end holder, such as by the use of a push wire which pushes the second stent end out of a hollow receptacle formed in the second stent end holder carried by the catheter shaft; the balloon may be reinflated before or after the release of the second stent end. The release of the ends of the stent and the inflation of the balloon causes the stent, and the graft when a stent graft is used, to be fully deployed. Thus the stent and graft material associated with the stent remain in place at the target site. The balloon is then deflated and the catheter shaft and balloon therewith are removed from within the stent. In some cases when a sheath is used, it may be desired to deploy the sheath over the deflated balloon prior to removing the balloon from within the stent.

One aspect of the invention relates to the use of an endoluminal prosthesis in which one portion of the prosthesis is engageable with a prosthesis holder carried by the catheter shaft, the portion being disengageable from the catheter shaft upon inflating the balloon. The prosthesis may be of the self-expanding, thermally-expanding or balloon-expandable type; in a preferred embodiment the prosthesis is a self-expanding, coil-type stent.

Another aspect of the invention relates to the prosthesis having first and second prosthesis portions secured to the catheter shaft so that they can be separately released from the catheter shaft. In particular, the first prosthesis portion is released by inflation of the balloon and the second prosthesis portion is selectively released by other than inflating the balloon.

A further aspect of the invention relates to a prosthesis having first and second prosthesis portions releasably secured to the catheter shaft. A sheath can be slidably mounted around the catheter shaft and be moveable between a first position surrounding the prosthesis and a second position spaced-apart from the prosthesis. The sheath, in its first position, aids delivery of the prosthesis to the target site. The sheath can also be used to cover the balloon after the prosthesis has been placed at the target site and the balloon has been deflated; this can aid removal of the catheter from the patient. The prosthesis is prevented from assuming its second, expanded-diameter state the sheath being in its first position surrounding the stent and by both the engagement of the first and second prosthesis portions with the catheter shaft. The sheath may be used to provide the release mechanism for the second prosthesis portion.

A still further aspect of the invention relates to a method for placing the prosthesis within a body. This aspect of the invention involves introducing the distal portion of a catheter at a target site within a body with an inflatable balloon surrounded by an endoluminal prosthesis at the distal portion. The balloon is then inflated thereby both expanding at least the first prosthesis portion and releasing the first prosthesis portion from the catheter shaft. The second prosthesis portion is then released by other than inflating the balloon. The balloon is deflated and the catheter shaft and the deflated balloon therewith are removed from within the stent leaving the expanded stent within the body. This procedure may be carried out with an introducer sheath at a first position surrounding the prosthesis during positioning of the prosthesis at the target site. The sheath would be moved to uncover the prosthesis prior to inflating the balloon. After the prosthesis is in place and the balloon is deflated, the sheath may be placed over the deflated balloon for removal from the body.

Other features and advantages of the invention will appear from the following description in which the preferred embodiments have been set forth in detail in conjunction with the accompanying drawings.

DESCRIPTION OF THE SPECIFIC EMBODIMENTS

Figures 1, 1A:
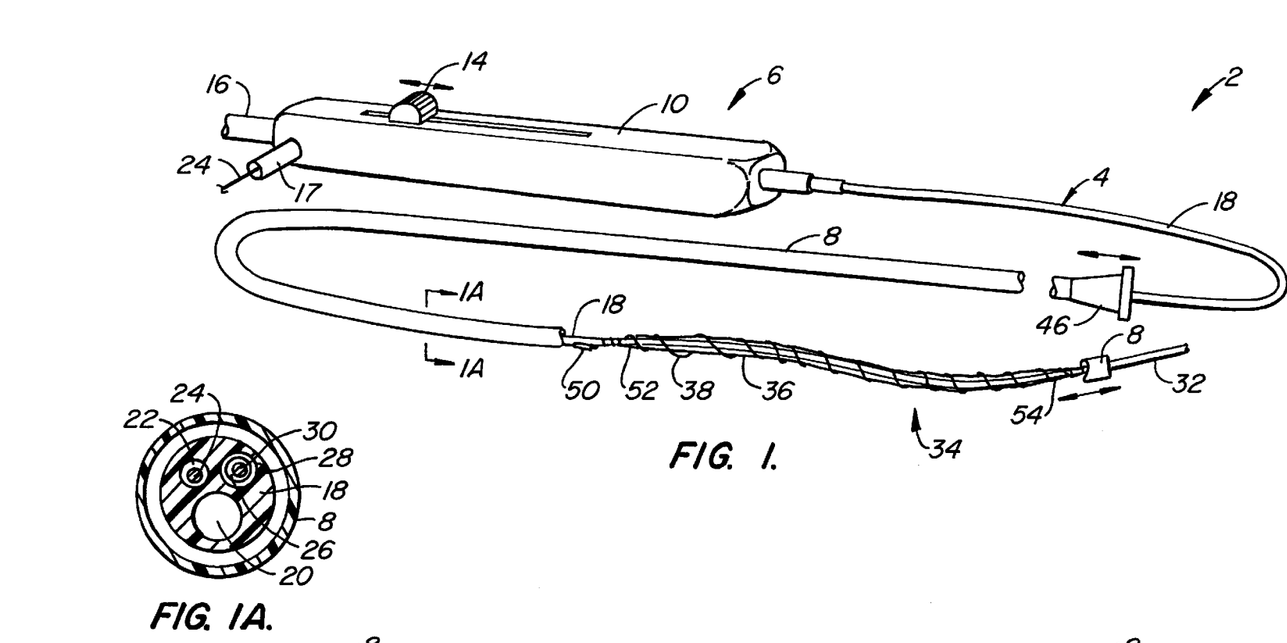
FIG. 1 is an overall view of a catheter assembly made according to the invention using a straight stent embodiment.
FIG. 1A is an enlarged cross-sectional view taken along line 1A—1A of FIG. 1.

FIG. 1 illustrates a catheter assembly 2 made according to the invention. Catheter assembly 2 includes broadly a catheter 4 extending from a proximal end adaptor 6, the catheter having an introducer sheath 8 slidably mounted over the catheter. Proximal end adaptor 6 includes a body 10 to which a push wire manipulator 14 is slidably mounted. Proximal end adaptor 6 also includes an inflation port 16, to permit a balloon, discussed below, to be inflated and deflated during use, and a guidewire port 17.

Figure 1B:
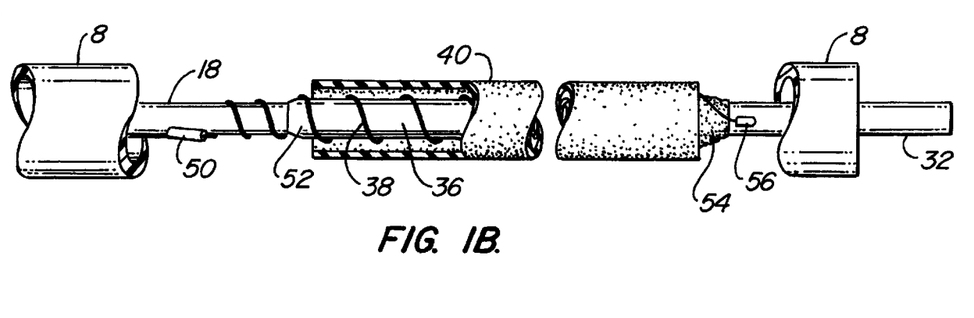
FIG. 1B is an enlarged simplified partial cross-sectional view of the distal portion of the catheter of FIG. 1, with the addition of an external graft, to illustrate the relative relationship between the various components.

Catheter 4 includes elongate catheter shaft 18 defining three lumens therein. FIG. 1A illustrates an inflation lumen 20, coupled to inflation port 16, a guidewire lumen 22 housing a guidewire 24, the proximal end of the guidewire passing through guidewire port 17. The catheter shaft 18 also includes a push wire lumen 26 housing a push wire tube 28, a push wire 30 being housed within push wire tube 28. Push wire 30 is connected to push wire manipulator 14 and is pushed and pulled through push wire tube 28 by the movement of manipulator 14. Push wire tube 28 is used to help prevent push wire 30 from buckling, which may occur during use due to the relatively thin diameter of the push wire, typically about 0.004 to 0.030 inch. The distal end of guidewire 24, not shown, is positioned near the tip 32 of catheter shaft 18 and is used to help guide tip 32 through the body, typically through blood vessels, as is conventional. During the typically percutaneous introduction of the distal portion 34 of catheter 4 into the vasculature, sheath 8 is in the distal position shown in FIG. 1 to cover up the balloon 36, stent 38, and graft 40 as shown in FIG. 1B.

Figures 2A, 2B, 2C, 2D:
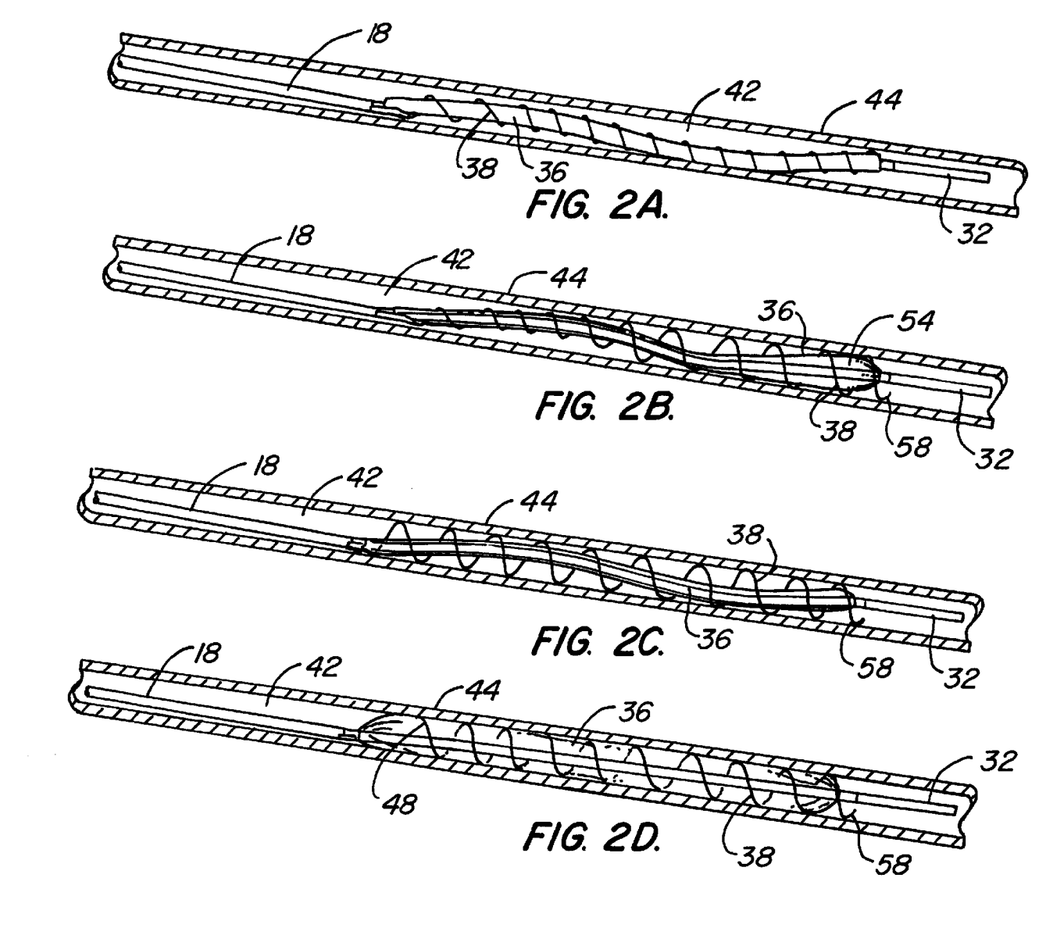
FIG. 2A illustrates the catheter of FIG. 1A introduced into a blood vessel at a target site after the sheath has been pulled back to expose the stent and balloon at the target site, the graft of FIG. 1B being omitted from FIGS. 2A–2G for clarity of illustration.
FIG. 2B is similar to FIG. 2A with the distal portion of the balloon partially inflated to cause the first, distal stent portion to disengage from the first stent portion holder.
FIG. 2C is similar to FIG. 2B but after the balloon has been deflated which permits. the distal portion of the stent to spin relatively freely and thus expand to press against the inside wall of the blood vessel.
FIG. 2D illustrates the balloon filly reinflated and showing the second, proximal end of the stent disengaged from the second stent end holder.

Once in position at the target site 42 in blood vessel 44, see FIG. 2A, handle 46 of introducer sheath 8 is pulled in a proximal direction to expose graft 40, stent 38, and balloon 36. Note that in FIGS. 2A–2F, graft 40 is not shown for clarity of illustration.

Stent 38 is a coil-type of stent typically made of 0.004 to 0.030 inch diameter Nitinol spring wire. Stent 38 may be made of other materials including stainless steel, ELGILOY®, a cobalt-chromium-nickel alloy made by Elgiloy Inc., and polymers. Stent 38, when in a relaxed state, typically has a diameter of about 2 to 30 mm to accommodate blood vessel 44 having an internal diameter of about 2 to 30 mm. The wire diameter, coil diameter, and other properties of stent 38 may vary according to the particular body region to be accessed and the procedure to be conducted. In FIGS. 1B and 2A, balloon 36 is in a deflated condition while stent 38 is in a first, reduced-diameter state with the coil-type stent 38 in torqued compression onto catheter shaft 18 and balloon 36. Stent 38 includes a proximal end 48, shown also in FIG. 3A, which is housed within a hollow interior of a stent end holder 50. Proximal end 48 of stent 38 can be selectively dislodged from proximal stent end holder 50 by the distal movement of push wire 30 through push wire tube 28. In this embodiment, proximal stent end holder 50 is an extension of push wire tube 28 as suggested in FIG. 3A. Instead of push wire 30, push wire tube 28 could be pulled into catheter shaft 18 to release proximal end 48 of stent 38.

It is typically desired that the length of stent 34 be about the same when in the reduced-diameter state as when in the relaxed, enlarged-diameter state. This is desirable to minimize shifting of the stent at the target site during deployment. The use of a coil-type stent helps to achieve this by permitting the appropriate spacing the turns of the stent onto the balloon-covered catheter shaft when in a reduced-diameter state. For example, stent 38 having a relaxed diameter of 6 mm, a relaxed length of 5 cm and 10 turns in a relaxed state, can be wound onto the balloon-covered catheter shaft to assume a reduced-diameter state with about 30 turns, a diameter of about 2.5 mm and the same length of about 5 cm. The results will vary depending on various factors, such as the pitch of the coil.

A proximal end 52 of balloon 36 is spaced-apart from stent end holder 50 by a distance sufficient to permit at least one turn, and preferably one-and-a-half to two turns, of stent 38 to be wrapped directly around catheter shaft 18 without any of balloon 38 being between stent 38 and catheter shaft 18. The purpose of this is to inhibit the dislodgrnent of proximal end 48 from stent end holder 50 upon the initial inflation of balloon 36 as will be discussed in more detail below. Thus, the initial turn or turns of stent 38 are in effective contact with catheter shaft 18 because there is no portion of balloon 36 between the turn or turns of the stent and the catheter shaft.

The distal end 54 of balloon 36 is positioned near the distal stent end holder 56. Accordingly, when the distal stent end 58 is engaged within distal stent end holder 56, stent 38 quickly starts wrapping around balloon 36. Thus, upon inflation of balloon 36, distal stent end 58 is pulled from distal end holder 56 as shown in FIG. 2B. Note that in FIG. 2B, balloon 36 is only partly inflated. Inflation of distal end 54 of balloon 36 is aided in this embodiment by somewhat more loosely wrapping stent 38 around the balloon at distal end 54 than over the remainder of the balloon. This reduces the resistance to inflation of the balloon at distal end 54 thus permitting the expansion of the distal end of stent 38 before expansion at its proximal end. Other ways to promote this initial expansion of distal end 54 of balloon 36, such as making distal end 54 easier to expand than the remainder of the balloon or only partially retracting sleeve 8 or using a balloon with separately inflatable proximal and distal portions, can be used.

After this partial expansion of balloon 36, the balloon is deflated as shown in FIG. 2C. This permits stent 38 to more freely expand within blood vessel 44 so that a greater portion of the stent is in its expanded state in FIG. 2C than in FIG. 2B. FIG. 2D illustrates balloon 36 after having been fully inflated and the dislodgment of proximal end 48 of stent 38 from proximal end stent holder 50 by moving push wire 30 distally through the manipulation of push wire manipulator 14. This dislodgment of proximal end 48 preferably occurs after the full inflation of balloon 36; it could also occur before the full inflation of the balloon as well.

Figure 2E:
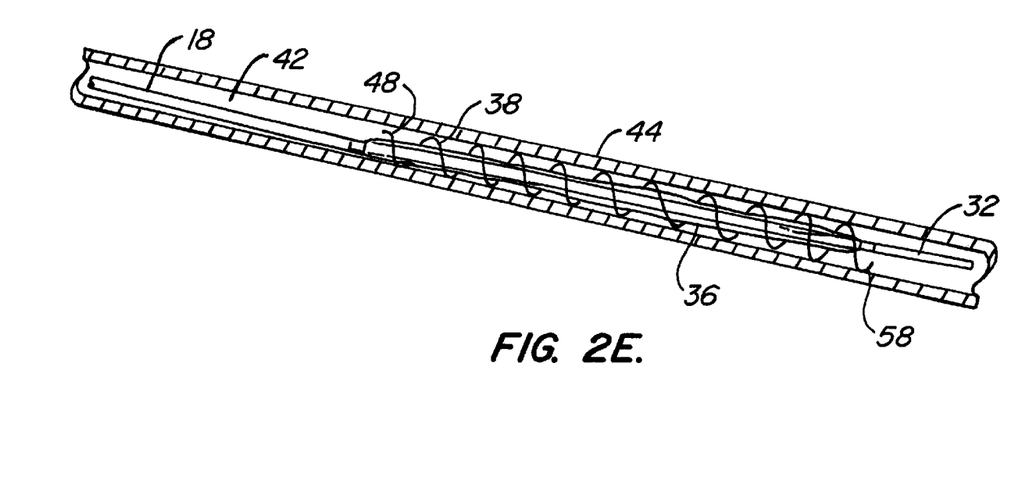
FIG. 2E is similar to FIG. 2D but with the balloon fully deflated.
Figure 2F:
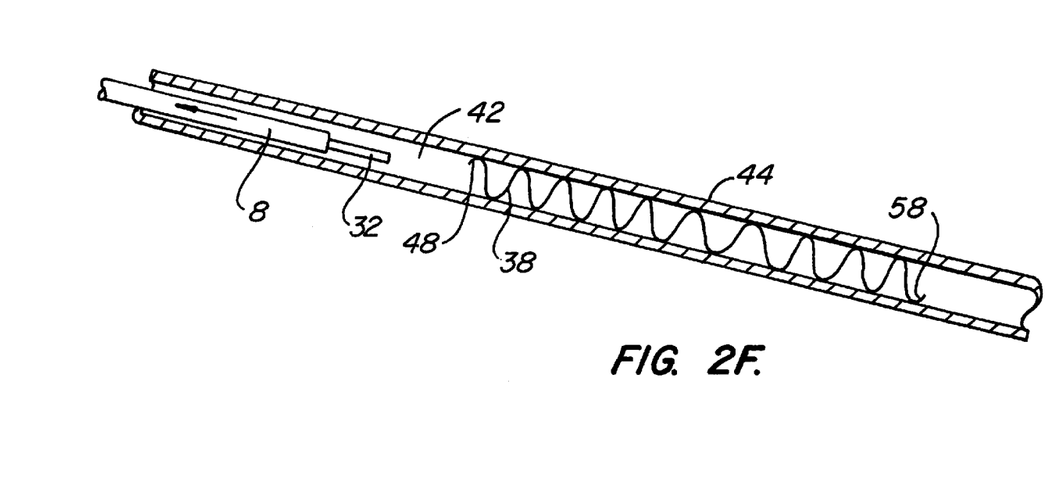
FIG. 2F shows the stent in its second, expanded-diameter state after withdrawal of the distal portion of the catheter shaft.
Figure 4A:
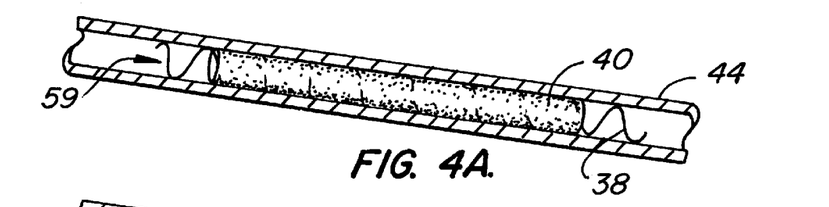
FIG. 4A illustrates the stent of FIG. 2G with the external graft of FIG. 1B surrounding the stent and held against the inner wall of the blood vessel by the stent.

FIG. 2E illustrates balloon 36 deflated leaving stent 38 in its expanded-diameter state pressing graft 40, not shown in FIGS. 2A–2F but shown in FIG. 4A, against the inner wall of blood vessel 44. Though not always necessary, it may be desired to move sheath 40 in a distal direction to cover balloon 36 prior to removing the distal portion of the catheter shaft. FIG. 2F illustrates stent 38 in its expanded-diameter state after removal of catheter shaft 18 and sheath 8. It can be noted that in FIGS. 1B and 4A the length of graft 40 is shorter than the length of stent 38; this helps to ensure that the ends of graft 40 are pressed against the interior of blood vessel 44.

In use, the user introduces distal portion 34 of catheter 4 into, for example, a suitable blood vessel 44 and directs tip 32 of catheter shaft 18 to a target site 42 using guidewire manipulator 12 and appropriate visualization techniques as is conventional. Balloon 36 is partially inflated through inflation port 16 to the condition of FIG. 2B causing distal stent end 58 to be dislodged from distal stent end holder 56. Balloon 36 is then deflated to permit a distal portion of stent 38 to more fully expand within blood vessel 44. Balloon 36 is then fully expanded as shown in FIG. 2D and push wire 30 is extended by moving push wire manipulator 14 in a distal direction causing proximal end 48 of stent 36 to be dislodged from proximal stent end holder 50; alternatively, push wire 30 could be extended to first dislodge proximal end 48 of stent 38B from proximal end stent holder 50 and then balloon 36 could be fully expanded. The inflation of balloon 36 also expands graft 40. Balloon 36 is then deflated as shown in FIG. 2E and withdrawn into sheath 8. A distal portion of catheter shaft 18 and balloon 36 therewith are then withdrawn from target site 42 in blood vessel 44 (see FIG. 2F) leaving stent 38 and graft 40, which together constitute a stent graft 59, in place as shown in FIG. 4A.

Figure 4B:
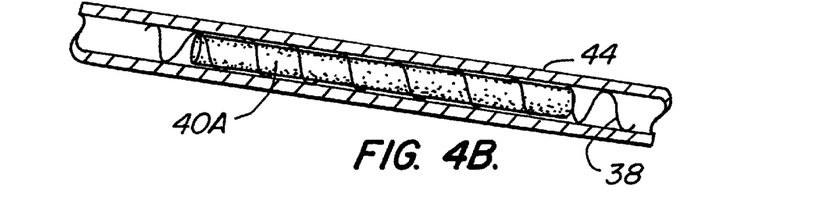
FIG. 4B illustrates the stent of FIG. 2G with an internal graft.

FIG. 4B illustrates an alternative embodiment in which graft 40A is an internal graft coupled to stent 38. One method of coupling internal graft 40A to stent 38 is through the use of one or more strips 60 of graft material. Pockets, not shown, are created between stent 40A and strips 60 to permit stent 38 to pass between the two. The gaps are relatively large to prevent graft 40A from being overly deformed during the deployment of the stent and graft.

Figures 4C, 4E:
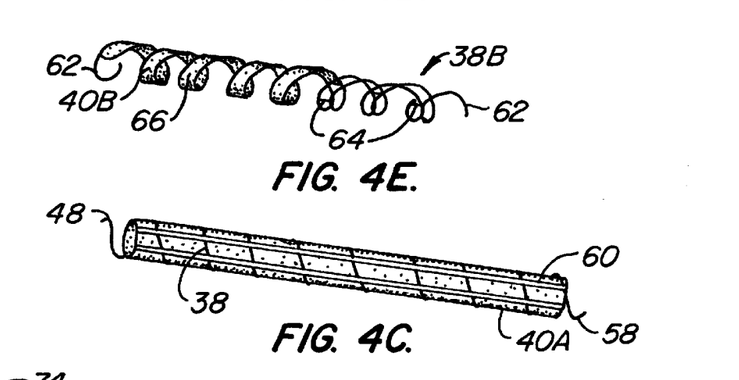
FIG. 4C illustrates fastening an internal graft to an external stent using strips of graft material creating pathways for the stent.
FIG. 4E illustrates a stent graft in which parallel stent wires are kept in a spaced-apart relationship by spacers, the coiled stent wires being covered on both the inside and the outside by graft material, only a portion of the stent of FIG. 4A shown covered by the graft material to illustrate the arrangement of the coiled stent wires and spacers.
Figure 4D:
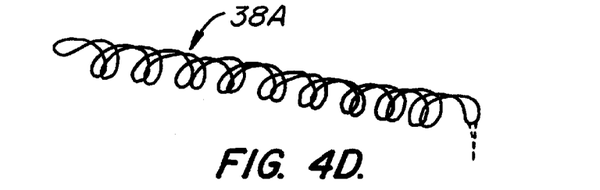
FIG. 4D illustrates an alternative coil-type stent in which the stent comprises a pair of spaced-apart coiled stent wires.

FIG. 4D illustrates a stent 38A made up of a pair of spaced-apart coiled stent wires joined together at their ends. To permit the ends of stent 38 to be secured to catheter shaft 18, the stent end holders could, for example, be modified to accommodate the generally U-shaped ends or the ends could be squeezed together or otherwise made to form a pointed end as suggested by the dashed lines at one end of stent end 38A.

FIG. 4E illustrates a presently preferred embodiment in which a stent 38B is made up of a pair of coiled stent wires 62 joined together and maintained in a spaced-apart relationship by spacer wires 64 to create a ladder-like stent 38B. A strip 66 of graft material is secured to coiled stent wire 62 to form a spiral graft 40B surrounding stent 38B to lie on both the inside and the outside of the stent. Only a portion of stent 38B is covered with strip 66 to illustrate the construction of the stent. Strip 66 of graft material can be adhered to stent 38B in a variety of ways including use of an adhesive, heat welding, or making strip 66 in the form of a tube or a double-sided strip with a hollow interior which encases coiled stent wires 62. It can be seen that only one of the two coiled stent wires 62 extend outwardly at each end of stent 38B to form the proximal end 48B and the distal end 58B of stent 38B.

Ladder-like stent 38B could also be made from a tube or sheet of stent material by, for example, stamping, laser cutting, waterjet cutting or other suitable processes. It is expected that processes which do not overly heat the stent material, such as waterjet cutting, may be preferred. The graft material can be in the form of a tube of graft material which is slid over ladder-like stent 38B and secured in place by, for example, suturing the ends of the graft material.

Figure 5:
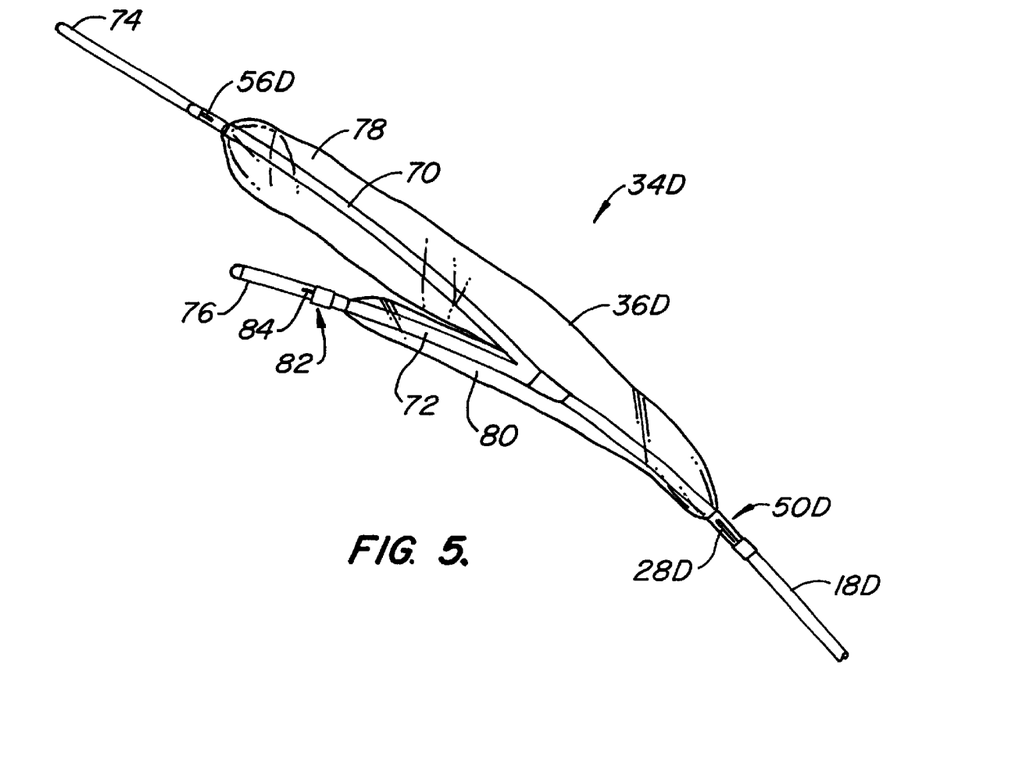
FIG. 5 shows a bifurcated version of the catheter and balloon allowing for deployment of a bifurcated prosthesis, the prosthesis not shown.

FIG. 5 shows a distal portion 34D of a bifurcated catheter made according to the invention with like reference numerals referring to like elements. Catheter shaft 18D includes first and second arms 70, 72 terminating at first and second tips 74, 76. In FIG. 5 neither a stent, shown in FIG. 6, nor graft material is illustrated for clarity of illustration. Balloon 36D is a bifurcated balloon having a first portion 78 extending along first arm 70 and a second portion 80 extending along second arm 72. Proximal stent end holder 50 is carried on catheter shaft 50D while distal stent end holder 56D is positioned along first arm 70D. The stent end holders 50D, 56D are similar to stent end holders 50, 56 illustrated in FIGS. 3A and 3B with the hollow tubular members extending distally for proximal stent end holder 50 and proximally for distal stent end holder 56D. A second distal stent end holder 82 is carried along second arm 72 and has a distally extending open-ended tube 84 corresponding to push wire tube 28D in that it also extends in a distal direction and uses a push wire to disengage the end of a stent from within the push wire tube 84. As discussed above, other methods for removing the ends of the stents from push wire tubes 28D, 84 such as retracting the push wire tubes proximally, could also be used.

Figure 3A:
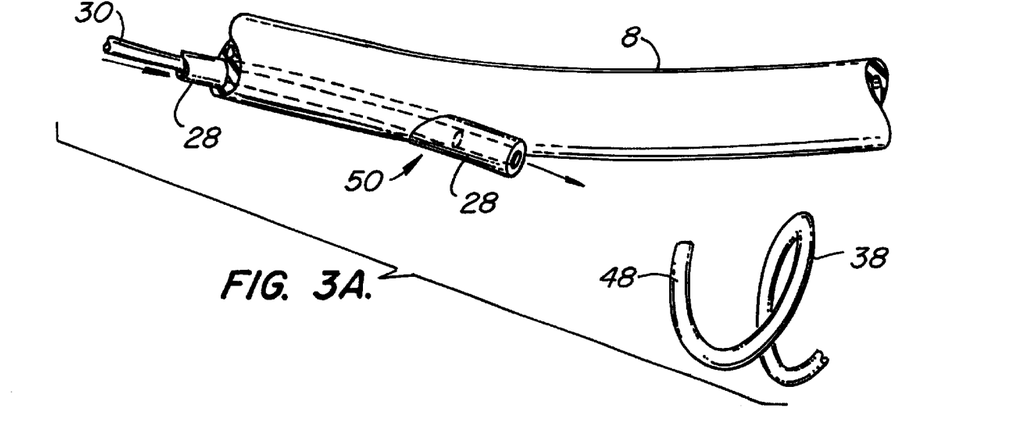
FIG. 3A is an enlarged view illustrating a push wire extending along the catheter shaft, passing through a push wire tube to permit the second, proximal end of the stent to be disengaged from the catheter shaft.
Figure 3B:
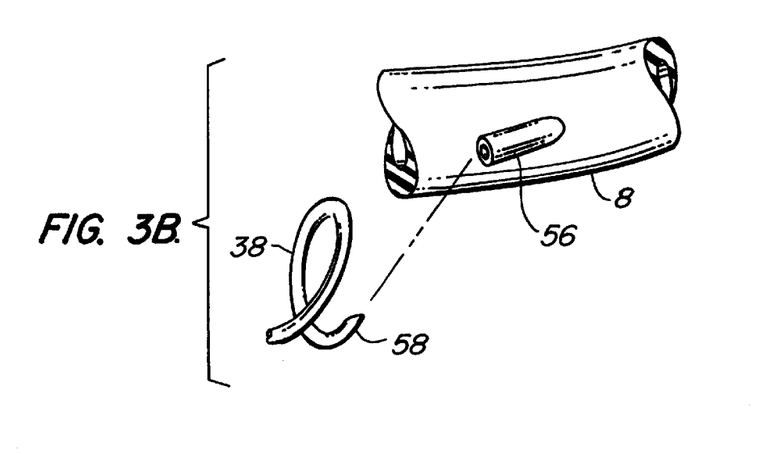
FIG. 3B illustrates the first stent end holder and the first, distal end of the stent which slidably engages an opening formed in the first stent end holder.
Figure 6:
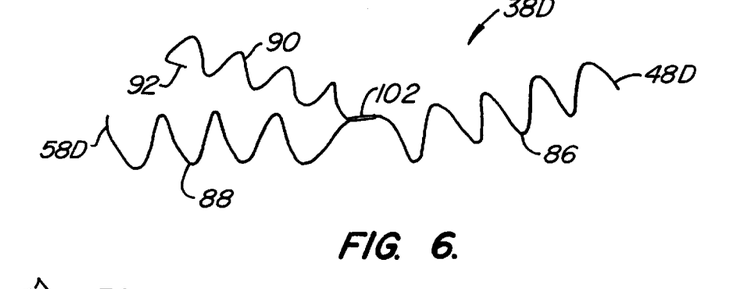
FIG. 6 illustrates a bifurcated stent.

FIG. 6 illustrates a bifurcated stent 38D having a main portion 86 and first and second arms 88, 90 which are wrapped around main portion of catheter shaft 18D and first and second arms 70, 72 respectively. Proximal end 48D of stent 38D corresponds to proximal end 48 of stent 38 as shown in FIG. 3A while distal end 58D of stent 38D corresponds to distal stent end 58 of stent 38 shown in FIG. 3D. Proximal and distal ends 48D, 58D engage proximal and distal stent end holders 50D, 56D in manner similar to those of FIGS. 3A and 3B. However, the distal end 92 of second arm 90 may have a reverse bend.

Figures 7, 7A:
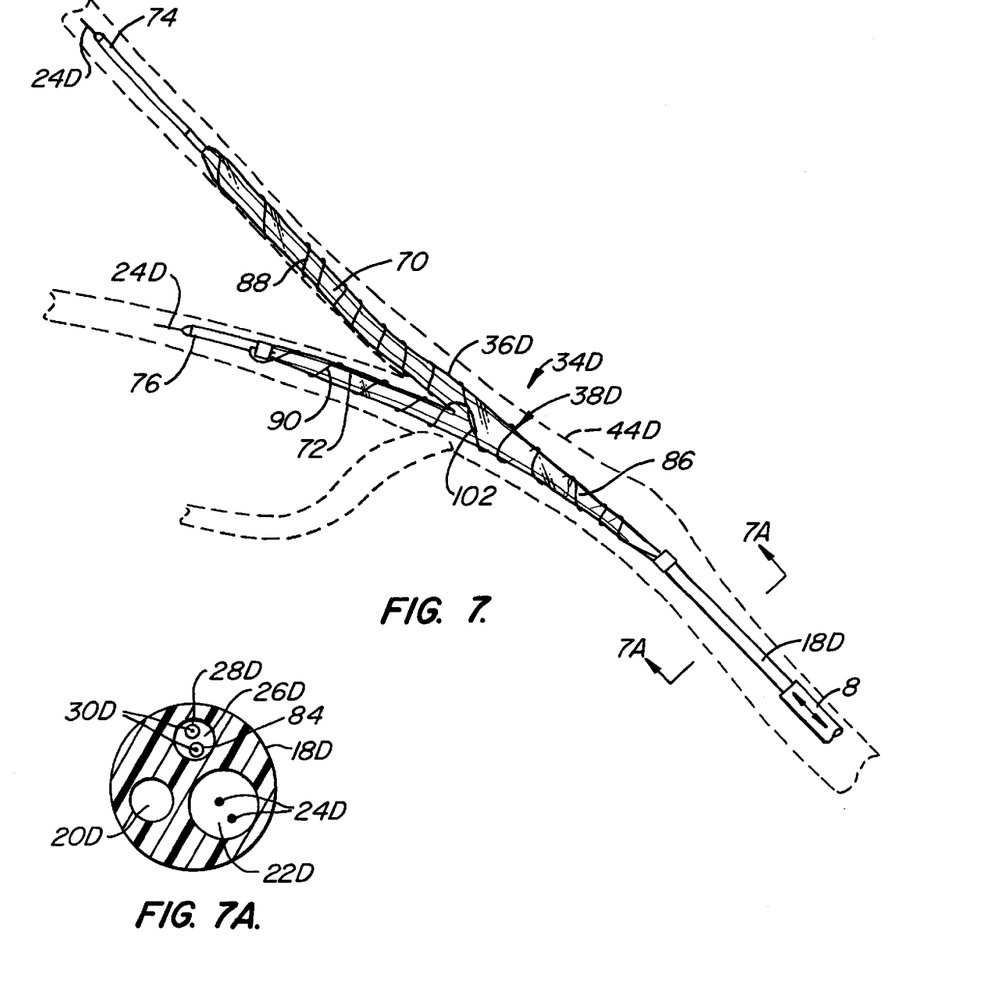
FIG. 7 shows the bifurcated stent of FIG. 6 loaded onto the bifurcated catheter of FIG. 5 with the balloon deflated.
FIG. 7A is an enlarged cross section of view taken along line 7A—7A of FIG. 7.

As shown in FIG. 7A, catheter shaft 18D defines three lumens, inflation lumen 20D, guidewire lumen 22D, housing tube guidewires 24D, one for each arm 70, 72, and a push wire lumen 26D housing push wire tubes 28, 84 with push wires 30D slidingly passing within the push wire tubes 28D, 84.

Figure 8:
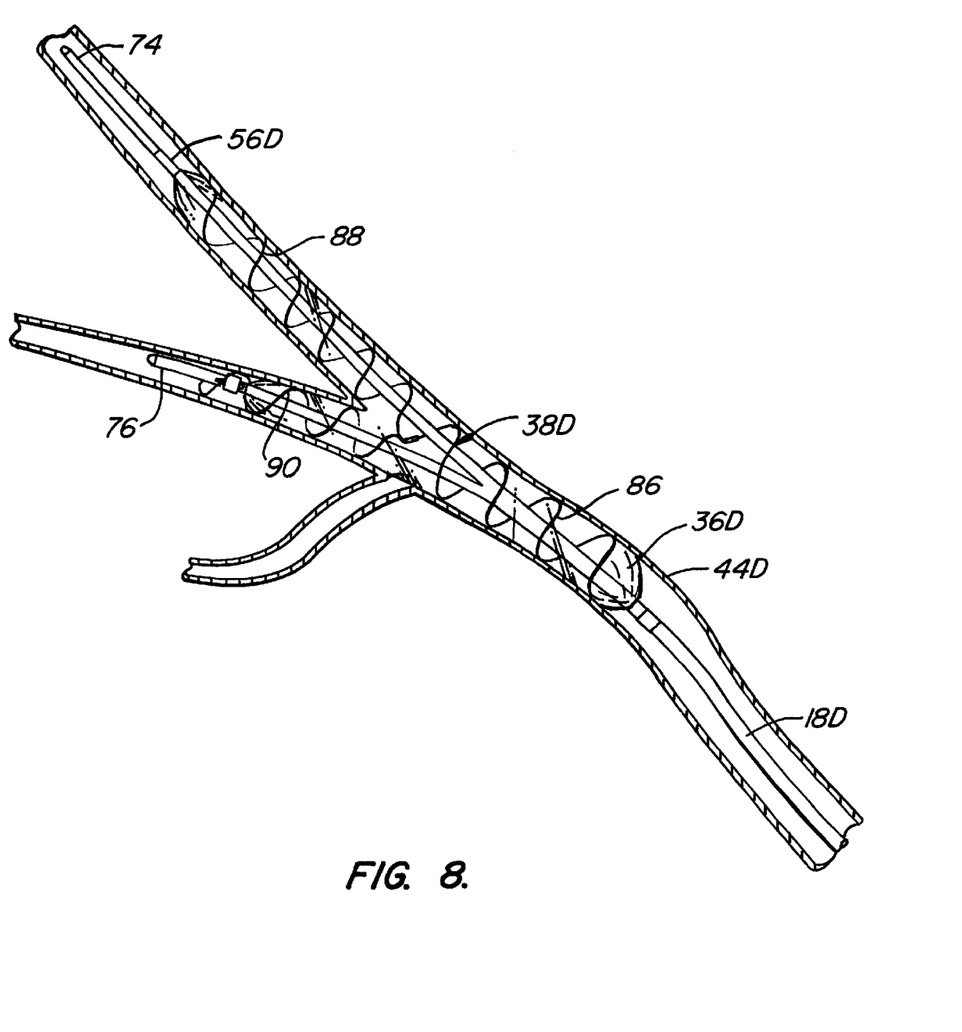
FIG. 8 shows the bifurcated stent of FIG. 7 deployed in a bifurcated vessel with the balloon inflated.
Figure 9:
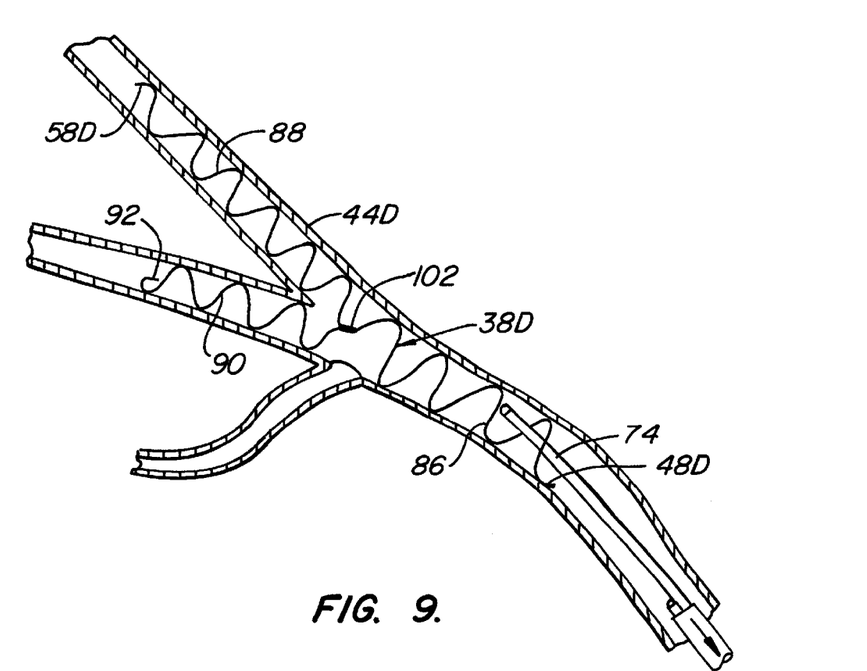
FIG. 9 shows the stent of FIG. 8 deployed in the vessel and the withdrawal of the catheter.

FIG. 7 illustrates distal catheter portion 34D with balloon 36D in a collapsed state, stent 38D wrapped around both balloon 36D and distal portion 34D, and showing the outline of a branched vessel 44D shown in dashed lines. Again, as with FIGS. 2A–2F, graft material is not shown for ease of illustration. However, as with the embodiments of FIGS. 1–4, graft material is typically used with stent 38D. Of course other types of stents, other than the coiled bifurcated stent shown in FIG. 6, could be used as well. The placement of stent 38D occurs in substantially the same fashion as can occur with the straight stent described above. The main difference is that proximal ends 48D and 92 of stent 38D are both released using push wires 30D while distal stent end 58D is released by the partial inflation of balloon 36D. FIG. 8 illustrates the result of having gone through the stent end release cycle, that is typically partial inflation, which releases stent end 58D, deflation and then the full inflation and release of stent ends 48D, 92. After stent 38D has been expanded, distal catheter portion 34D and balloon 36D therewith are removed from the bifurcated target site as suggested in FIG. 9. Again, graft material is not shown for clarity of illustration. As with the above embodiments, graft material may not be, but often is, used with the stent or other prosthesis.

Figure 10:
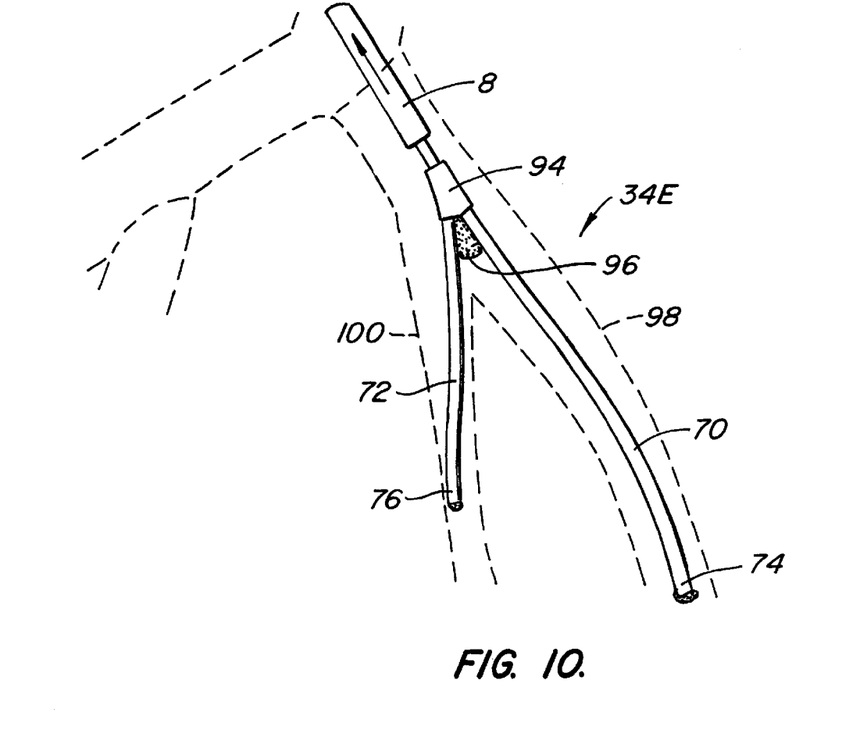
FIG. 10 shows a bifurcated catheter with a spring member used to keep the catheter ties apart.

FIG. 10 illustrates a distal catheter portion 34E similar to that shown in FIG. 5 in which the first and second arms 70, 72 are biased outwardly at their junction 94 by a biasing element 96 which tends to separate arms 70, 72 from one another. Biasing element may be made of a variety of materials, such as a leaf spring or, as illustrated, a triangular section of a resilient spongy material such as silicone or polyurethane. Using biasing element 96 helps to ensure arms 70, 72 are directed down different vascular segments 98, 100. To do so distal catheter portion 34E is typically housed within sheath 8 until just above the target site. At that point, distal portion 34E is extended out through the open distal end of introducer sheath 8 permitting arms 70, 72 to move freely into vascular segments 98, 100. This movement may be aided using guidewires 24D in addition to biasing element 96.

Modifications and variation may be to the above-described catheter assembly and method may be made without departing from the subject of the invention as defined in the following claims. For example, it may not be necessary to only partly inflate the balloon as indicated in FIG. 2B; rather, it may be desired to fully inflate the balloon to release distal stent end 58 from distal stent end holder 56. Also, it may not be necessary to deflate the balloon after the full or partial inflation of the balloon as shown in FIG. 2C. In a preferred embodiment, a coiled stent is placed in torqued compression onto the catheter shaft and balloon. Other types of radially expanding stents, which may or may not be self-expanding, can be used as well. For example, tubes of stent material having numerous axially extending slits which permit the tube to be expanded radially in a diamond-like pattern using the balloon can be used. The stent could also be made of a temperature-sensitive shape-memory material. In the preferred embodiment, balloon 36 is necessary to expand graft 40 from its reduced-diameter state of FIG. 1B to its expanded-diameter state of FIG. 4A; graft material may be used which does not require a balloon to place it into its fully expanded condition. In the preferred embodiment, graft 40 is an expandable, porous PTFE graft material such as that available from IMPRA, Baxter, W. L. Gore or Atrium. Other types of graft material, such as polyester or polyurethane, can be used. Instead of mechanically releasing proximal end 48 of stent 38, the proximal end can be held and selectively released by electrolytic methods as shown in U.S. Pat. No. 5,122,136 to Guglielmi, et al. Distal stent end 58 could be releasably coupled to catheter shaft 18 for release by inflation of balloon 36 by other than holder 56, such as through a releasable or breakable tether, a clip or other fastner, adhesive or other releasable or breakable structure. The holding and selective release of proximal stent end 48 could be by using a range of conventional or unconventional holders; for example, the distal end of sheath 8 could be left to cover the proximal end 52 of balloon 36 during the initial inflation of balloon and then pulled back to uncover the proximal balloon end for the subsequent inflation of the balloon. Pull or push wires could be used to actuate a catch to release proximal stent end 48. Conventional techniques, such as those shown in U.S. Pat. Nos. 5,372,600; 5,476,505; 5,683,451; 5,443,500; 4,913, 141; 5,246,445; 5,360,401; 5,201,757; 4,875,480; 4,848, 343; 4,732,152; and 4,665,918, and those shown in WO 97/07756 and WO 94/16629, may also be used to release proximal stent end 48.

Bifurcated embodiments have been shown illustrating use of a single balloon. If desired, a number of separate balloons could be used instead of a single balloon. For example, three separate balloons could be used, one for each branch of the stent. The three balloons could be all coupled to a single inflation lumen; in such case the three separate balloons would act similarly to the single balloon. However, if each balloon were separately inflatable, more than one of the stent ends could be released through the inflation of the various balloons. Stent 38D is shown with main portion 86 and first and second arms 88, 90 secured together at a common location 102. It may be desired to have, for example, second arm 90 be joined to a section of stent 38D between main portion 86 and first arm 88 by a sliding connection; this may be useful to help properly seat or orient the stent or a stent graft within the bifurcated vessel. First arm 88 is shown as a single continuous coil in FIG. 6. If desired, first arm 88 could include one or more separate sections of stent to create the first arm. Instead of having a single catheter split into two catheter arms, second arm 72 could actually be a separate catheter extending through the interior of catheter shaft 18D; this would facilitate inflating a balloon associated with the second arm separately from the one or more other balloons associated with the main portion of the catheter shaft and the first arm. It may also permit the second arm of the catheter shaft to move longitudinally relative to the main catheter shaft and the first arm of the catheter shaft.

Any and all patents, applications, and printed publications referred to above are incorporated by reference.

What is claimed is:

1. A catheter including a catheter shaft with a distal portion, an inflatable balloon at the distal portion, the balloon surrounded by an expandable endoluminal prosthesis, the improvement comprising:

the prosthesis having first and second prosthesis portions releasably secured to the catheter shaft;

means for releasing the first prosthesis portion from the catheter shaft by inflating the balloon while the second portion remains unreleased; and means for selectively releasing the second prosthesis portion from the catheter shaft by other than inflating the balloon.

2. A catheter including a catheter shaft with a distal portion, an inflatable balloon at the distal portion, the balloon surrounded by an expandable endoluminal prosthesis, the improvement comprising:

the prosthesis having first and second prosthesis portions;

the catheter shaft comprising first and second prosthesis portion holders;

the prosthesis capable of assuming a second, expanded-diameter state from a first, reduced-diameter state;

a sheath slidably mounted around the catheter shaft;

the first and second prosthesis portions being releasably secured to the catheter shaft by the first and second prosthesis portion holders, said first portion being releasable from the catheter shaft by inflating the balloon while the second prosthesis portion remains unreleased; and said sheath being movable between a first position surrounding said prosthesis and a second position spaced-apart from said prosthesis;

whereby said prosthesis is prevented from assuming its second, expanded-diameter state by (1) the engagement of the first and second prosthesis portions with the first and second prosthesis portion holders, and (2) the sheath being in its first position.

3. A catheter comprising:

a catheter shaft having a distal portion;

an inflatable balloon mounted to the distal portion and inflatable from a deflated condition to an inflated condition;

an endoluminal prosthesis, capable of assuming a second, expanded-diameter state from a first, reduced-diameter state, surrounding the balloon in the first, reduced-diameter state;

the distal portion of the catheter shaft having a first prosthesis portion holder and a second prosthesis portion holder; and the prosthesis having a first portion releasably engagable with the first prosthesis portion holder and a second prosthesis portion releasably engagable with the second prosthesis portion holder, said first portion being releasable from the catheter shaft by placing the balloon in the inflated condition while the second prosthesis portion remains unreleased.

4. The catheter according to claim 1 wherein the prosthesis comprises a stent.

5. The catheter according to claim 4 wherein the stent is a self-expanding stent.

6. The catheter according to claim 1 wherein the first portion is slidably engagable with the catheter shaft through the first prosthesis portion holder.

7. The catheter according to claim 1 further comprising:

a user-controlled release mechanism, operably coupled to the second prosthesis portion holder, by which a user can selectively disengage the second prosthesis portion from the catheter shaft by other than inflating the balloon.

8. The catheter according to claim 7 wherein the user-controlled release mechanism is a mechanical, user-controlled release mechanism.

9. The catheter according to claim 7 further comprising a sheath slidably mounted around the catheter shaft, said sheath movable between a first position surrounding said prosthesis and a second position spaced-apart from said prosthesis, whereby said prosthesis is prevented from assuming its second, expanded-diameter state by (1) the engagement of the first and second prosthesis portions with the catheter shaft through the first and second prosthesis portion holders, and (2) the sheath being in its first position.

10. The catheter according to claim 1 wherein said prosthesis has first and second distal ends and said first and second prosthesis portions are at said first and second distal ends.

11. The catheter according to claim 1 wherein the first prosthesis portion holder defines an elongate opening into which the first stent portion is slidably housed.

12. The catheter according to claim 1 wherein the balloon surrounds the distal portion.

13. The catheter according to claim 1 wherein the first prosthesis portion holder is free of overlying balloon material.

14. The catheter according to claim 1 wherein the prosthesis is a straight prosthesis.

15. The catheter according to claim 1 wherein the prosthesis is a bifurcated prosthesis having first and second arms.

16. The catheter according to claim 15 further comprising a biasing element coupled to the first and second arms biasing said arms away from one another.

17. The catheter according to claim 1 wherein the prosthesis is a coil-type stent having first and second ends.

18. The catheter according to claim 17 wherein the coil-type stent is in coiled, torqued compression in the first, reduced-diameter state.

19. The catheter according to claim 17 wherein the first end of the coil-type stent constitutes the first stent portion and the first stent portion holder has a hollow interior which is sized for receipt of the first end of the coil-type stent.

20. The catheter according to claim 17 wherein the second stent portion holder is configured for receipt of the second end of the coil-type stent.

21. The catheter according to claim 20 further comprising an elongate element, extending along the catheter shaft, having a distal portion operably engagable with the second end of the coil-type stent to permit a user to mechanically disengage said second end from the second stent portion holder.

22. The catheter according to claim 20 wherein said coil-type stent comprises a plurality of turns, at least one turn effectively directly contacting the catheter shaft between the second stent portion holder and the balloon.

23. The catheter according to claim 19 wherein the second prosthesis portion holder is positioned proximally of the balloon.

24. The catheter according to claim 1 further comprising a graft material associated with the prosthesis.

25. The catheter according to claim 24 wherein the graft material comprises a selected one of a strip or tube of the graft material.

26. The catheter according to claim 25 wherein the graft is positioned within the prosthesis.

27. The catheter according to claim 25 wherein the graft material comprises a chosen one of porous PTFE or ePTFE.

28. The catheter according to claim 25 further comprising a strip of material securing the stent and the graft to one another.

29. The catheter according to claim 1 further comprising a manipulator element extending along the catheter shaft and coupled to the distal portion to permit the distal portion to be steered.

30. The catheter according to claim 1 wherein the prosthesis comprises a coiled stent covered by a graft material to create a coiled stent graft with gaps between adjacent turns thereof.

31. The catheter according to claim 30 wherein said gaps and said turns both have longitudinal dimensions, said longitudinal dimensions of said gaps being at least as great as the longitudinal dimensions of the turns.

32. The catheter according to claim 30 wherein the coiled stent graft comprises a ladder-like stent with the edge elements comprising side rail elements and connector elements, connecting the edge elements, comprising rung elements.

33. A method for placing an endoluminal prosthesis within a body comprising:

introducing a distal portion of a catheter at a chosen position within a body, the distal catheter portion comprising an inflatable balloon surrounded by a prosthesis, first and second prosthesis portions of the prosthesis releasably secured to the catheter shaft at first and second positions along the catheter shaft;

inflating the balloon thereby releasing the first prosthesis portion from the catheter shaft while the second prosthesis portion remains secured to the catheter shaft;

releasing the second prosthesis portion from the catheter shaft by other than inflating the balloon;

deflating the balloon; and removing the catheter shaft and the deflated balloon therewith from the body leaving the expanded prosthesis within the body.

34. The method according to claim 33 wherein the inflating step comprises the step of expanding at least the first prosthesis portion.

35. The method according to claim 33 wherein the introducing step is carried out within a blood vessel.

36. The method according to claim 33 wherein the introducing step is carried out using a catheter in which the distal portion of the catheter comprises a generally Y-shaped catheter shaft, balloon and stent at a generally Y-shaped region within the body.

37. The method according to claim 33 wherein the introducing step is carried out with the chosen position being along a straight section of a blood vessel.

38. The method according to claim 33 wherein the inflating step is carried out by:

partially inflating the balloon causing the first stent portion to release from the catheter shaft; and then at least partially deflating the balloon; and then at least partially inflating the balloon.

39. The method according to claim 33 wherein the first prosthesis portion releasing step is carried out by the inflation of the balloon causing the first prosthesis portion to pull out of a first receptacle at the first position.

40. The method according to claim 33 wherein the second prosthesis portion releasing step is carried out by mechanically releasing the second prosthesis portion from the catheter shaft.

41. The method according to claim 40 wherein the mechanically releasing step is carried out after the first prosthesis portion releasing step.

42. The method according to claim 40 wherein the mechanically releasing step comprises longitudinally moving a releaser along the catheter shaft causing a distal end of the release wire to push the second prosthesis portion from a second receptacle at the second position along the catheter shaft.

43. The method according to claim 33 further comprising pulling a sheath, initially surrounding the balloon and prosthesis, from the balloon and prosthesis after the introducing step.

44. The method according to claim 43 further comprising pushing the sheath over the balloon prior to the removing step to facilitate the removing step.

45. The method according to claim 33 wherein the introducing step is carried out with the prosthesis comprising a graft material associated with a stent.

46. The method according to claim 45 wherein the introducing step is carried out with a tube of the graft material positioned generally concentrically with regard to the stent.

47. The method according to claim 46 wherein the introducing step is carried out with the tube of graft material surrounding the stent.

48. A catheter comprising:

a catheter shaft having a distal portion;

an inflatable balloon mounted to the distal portion and inflatable from a deflated condition to an inflated condition;

an endoluminal prosthesis, capable of assuming a second, expanded-diameter state from a first, reduced-diameter state, surrounding the balloon in the first, reduced-diameter state;

the distal portion of the catheter shaft having a first prosthesis portion holder;

the prosthesis having a first portion releasably engagable with the first prosthesis portion holder, said first portion being releasable from the catheter shaft when the balloon is placed in the inflated condition;

a second prosthesis portion holder, the prosthesis comprising a second portion releasably engaging the catheter shaft through the second prosthesis portion holder;

a user-controlled release mechanism, operably coupled to the second prosthesis portion holder, by which a user can selectively disengage the second prosthesis portion from the catheter shaft by other than inflating the balloon; and a sheath slidably mounted around the catheter shaft, said sheath movable between a first position surrounding said prosthesis and a second position spaced-apart from said prosthesis, whereby said prosthesis is prevented from assuming its second, expanded-diameter state by (1) the engagement of the first and second prosthesis portions with the catheter shaft through the first and second prosthesis portion holders, and (2) the sheath being in its first position.

49. A catheter comprising:

a catheter shaft having a distal portion;

an inflatable balloon mounted to the distal portion and inflatable from a deflated condition to an inflated condition;

a coil-type stent having first and second ends, capable of assuming a second, expanded-diameter state from a first, reduced-diameter state, surrounding the balloon in the first, reduced-diameter state;

the distal portion of the catheter shaft having a hollow interior sized for receipt of the first end of the stent;

the first end of the stent releasably engagable with the hollow interior, said first end being releasable from the catheter shaft when the balloon is placed in the inflated condition;

the distal portion of the catheter shaft having a second stent portion holder configured for receipt of the second end of the stent; and an elongate element, extending along the catheter shaft, having a distal portion operably engagable with the second end of the stent to permit a user to mechanically disengage said second end from the second stent portion holder.

50. A method for placing an endoluminal prosthesis within a body comprising:

introducing a distal portion of a catheter along a straight section of a blood vessel within a body, the distal catheter portion comprising an inflatable balloon surrounded by a prosthesis, first and second prosthesis portions of the prosthesis releasably secured to the catheter shaft at first and second positions along the catheter shaft;

inflating the balloon thereby releasing the first prosthesis portion from the catheter shaft;

releasing the second prosthesis portion from the catheter shaft by other than inflating the balloon;

deflating the balloon; and removing the catheter shaft and the deflated balloon therewith from the body leaving the expanded prosthesis within the body.

51. A method for placing an endoluminal prosthesis within a body comprising:

introducing a distal portion of a catheter at a chosen position within a body, the distal catheter portion comprising an inflatable balloon surrounded by a prosthesis, first and second prosthesis portions of the prosthesis releasably secured to the catheter shaft at first and second positions along the catheter shaft;

partially inflating the balloon causing the first prosthesis portion to release from the catheter shaft;

then at least partially deflating the balloon;

then at least partially inflating the balloon;

releasing the second prosthesis portion from the catheter shaft by other than inflating the balloon;

deflating the balloon; and removing the catheter shaft and the deflated balloon therewith from the body leaving the expanded prosthesis within the body.

52. A method for placing an endoluminal prosthesis within a body comprising:

introducing a distal portion of a catheter at a chosen position within a body, the distal catheter portion comprising an inflatable balloon surrounded by a prosthesis, first and second prosthesis portions of the prosthesis releasably secured to the catheter shaft at first and second positions along the catheter shaft;

inflating the balloon which causes the first prosthesis portion to pull out of a first receptacle at the first position, thereby releasing the first stent portion from the catheter shaft;

releasing the second prosthesis portion from the catheter shaft by other than inflating the balloon;

deflating the balloon; and removing the catheter shaft and the deflated balloon therewith from the body leaving the expanded prosthesis within the body.

53. A method for placing an endoluminal prosthesis within a body comprising:

introducing a distal portion of a catheter at a chosen position within a body, the distal catheter portion comprising an inflatable balloon surrounded by a prosthesis, first and second prosthesis portions of the prosthesis releasably secured to the catheter shaft at first and second positions along the catheter shaft;

inflating the balloon thereby releasing the first prosthesis portion from the catheter shaft;

longitudinally moving a release wire along the catheter shaft causing a distal end of the release wire to push the second prosthesis portion from a second receptacle at the second position along the catheter shaft, thereby releasing the second prosthesis portion from the catheter shaft;

deflating the balloon; and removing the catheter shaft and the deflated balloon therewith from the body leaving the expanded prosthesis within the body.

54. A method for placing an endoluminal prosthesis within a body comprising:

introducing a distal portion of a catheter at a chosen position within a body, the distal catheter portion comprising an inflatable balloon surrounded by a prosthesis, first and second prosthesis portions of the prosthesis releasably secured to the catheter shaft at first and second positions along the catheter shaft;

pulling a sheath, initially surrounding the balloon and prosthesis, from the balloon and prosthesis after the introducing step;

inflating the balloon thereby releasing the first prosthesis portion from the catheter shaft;

releasing the second prosthesis portion from the catheter shaft by other than inflating the balloon;

deflating the balloon; and removing the catheter shaft and the deflated balloon therewith from the body leaving the expanded prosthesis within the body.

55. The method according to claim 54, further comprising pushing the sheath over the balloon prior to the removing step to facilitate the removing step.

* * * * *